United States Patent
Rollins

(10) Patent No.: US 11,415,859 B2
(45) Date of Patent: Aug. 16, 2022

(54) METHODS AND APPARATUS FOR DETECTING NITRIC OXIDE

(71) Applicant: NATIONAL OCEANIC AND ATMOSPHERIC ADMINISTRATION, Silver Spring, MD (US)

(72) Inventor: Andrew Rollins, Boulder, CO (US)

(73) Assignee: UNITED STATES OF AMERICA, AS REPRESENTED BY THE SECRETARY OF COMMERCE, Silver Spring, MD (US)

( * ) Notice: Subject to any disclaimer, the term of this patent is extended or adjusted under 35 U.S.C. 154(b) by 197 days.

(21) Appl. No.: 16/913,088

(22) Filed: Jun. 26, 2020

(65) Prior Publication Data

US 2021/0405501 A1 Dec. 30, 2021

(51) Int. Cl.
*G02F 1/35* (2006.01)
*H01S 3/067* (2006.01)
(Continued)

(52) U.S. Cl.
CPC ............ *G02F 1/353* (2013.01); *G01N 21/64* (2013.01); *G01N 33/0037* (2013.01);
(Continued)

(58) Field of Classification Search
CPC ...... G02F 1/3501; G02F 1/3507; G02F 1/353; G02F 1/354; G02F 1/3551; H01S 3/0092;
(Continued)

(56) References Cited

U.S. PATENT DOCUMENTS

| | | | | |
|---|---|---|---|---|
| 3,891,848 A | * | 6/1975 | Fletcher | G01N 21/64 250/338.5 |
| 5,451,787 A | * | 9/1995 | Taylor | G01N 21/39 250/338.5 |
| 9,952,190 B2 | * | 4/2018 | Cogill | G01N 1/2273 |

FOREIGN PATENT DOCUMENTS

| | | | | |
|---|---|---|---|---|
| CN | 202974863 U | * | 6/2013 | |
| JP | 2003043005 A | * | 2/2003 | G01N 27/41 |

OTHER PUBLICATIONS

W. J. Bloss, T. J. Gravestock, D. E. Heard, T. Ingham, G. P. Johnson, and J. D. Lee, "Application of a compact all solid-state laser system to the in situ detection of atmospheric OH, HO2, NO and IO by laser-induced fluorescence," J. Environ. Monit., vol. 5, No. 1, pp. 21-28, Jan. 2003.

(Continued)

*Primary Examiner* — Daniel Petkovsek

(57) ABSTRACT

Embodiments of the present invention relate to methods and apparatus for detecting atmospheric nitric oxide (NO) at signal levels capable of distinguishing the NO isotopologues. More particularly, embodiments of the present invention relate to methods and apparatus for a single photon laser induced fluorescence (LIF) sensor that pumps a vibronic transition near 215 nm and observes the resulting red shifted fluorescence from about 255 to about 267 nm. Embodiments of the present system uses a NO-LIF measurement fiber-amplified laser apparatus capable of: generating laser linewidth that is sufficiently narrow to resolve the Doppler broadened NO spectrum at room temperature and thereby achieve high signal levels and distinguish the NO isotopologues; generating laser repetition rate sufficient to enable single-photon counting of the fluorescence signal; and having size, weight and environmental robustness allowing for integration onto airborne platforms.

20 Claims, 12 Drawing Sheets

(51) Int. Cl.
| | |
|---|---|
| *H01S 3/00* | (2006.01) |
| *G02B 27/28* | (2006.01) |
| *G01N 33/00* | (2006.01) |
| *G01N 21/64* | (2006.01) |
| *G02F 1/355* | (2006.01) |
| *G02F 1/39* | (2006.01) |

(52) U.S. Cl.
CPC ......... *G02B 27/286* (2013.01); *G02F 1/3501* (2013.01); *G02F 1/3551* (2013.01); *H01S 3/0092* (2013.01); *H01S 3/06754* (2013.01); *G01N 2201/0612* (2013.01); *G02F 1/354* (2021.01); *G02F 1/3507* (2021.01); *G02F 1/392* (2021.01)

(58) Field of Classification Search
CPC .. H01S 3/06754; G02B 27/286; G01N 21/64; G01N 33/0037; G01N 2201/0612
See application file for complete search history.

(56) References Cited

OTHER PUBLICATIONS

J. Bradshaw et al., "Observed distributions of nitrogen oxides in the remote free troposphere from the Nasa Global Tropospheric Experiment Programs," Rev. Geophys., vol. 38, No. 1, pp. 61-116, Feb. 2000.
J. D. Bradshaw, M. O. Rodgers, and D. D. Davis, "Single photon laser-induced fluorescence detection of NO and SO2 for atmospheric conditions of composition and pressure," Appl. Opt., vol. 21, No. 14, p. 2493, Jul. 1982.
J. D. Bradshaw, M. O. Rodgers, S. T. Sandholm, S. Kesheng, and D. D. Davis, "A two-photon laser-induced fluorescence field instrument for ground-based and airborne measurements of atmospheric NO.," J. Geophys. Res., vol. 90, No. D7, pp. 12861-12873, 1985.
M. Cazorla, G. M. Wolfe, S. A. Bailey, A. K. Swanson, H. L. Arkinson, and T. F. Hanisco, "A new airborne laser-induced fluorescence instrument for in situ detection of formaldehyde throughout the troposphere and lower stratosphere," Atmos. Meas. Tech., vol. 8, No. 2, pp. 541-552, 2015.
R. C. Cohen et al., "Quantitative constraints on the atmospheric chemistry of nitrogen oxides: An analysis along chemical coordinates," J. Geophys. Res. Atmos., vol. 105, No. D19, pp. 24283-24304, Oct. 2000.
J. D. Crounse, L. B. Nielsen, S. Jørgensen, H. G. Kjaergaard, and P. O. Wennberg, "Autoxidation of organic compounds in the atmosphere," J. Phys. Chem. Lett., vol. 4, No. 20, pp. 3513-3520, 2013.
J. Danielak, U. Domin, R. Kepa, M. Rytel, and M. Zachwieja, "Reinvestigation of the Emission γ Band System (A2Σ+–X2π) of the NO Molecule," J. Mol. Spectrosc., vol. 181, No. 2, pp. 394-402, Feb. 1997.
J. W. Drummond, A. Volz, and D. H. Ehhalt, "An optimized chemiluminescence detector for tropospheric NO measurements," J. Atmos. Chem., vol. 2, No. 3, pp. 287-306, Feb. 1985.
D. W. Fahey et al., "In situ measurements constraining the role of sulphate aerosols in mid-latitude ozone depletion," Nature, vol. 363, No. 6429, pp. 509-514, Jun. 1993.
D. Fittschen et al., "ROOOH: a missing piece of the puzzle for OH measurements in low-NO environments?," Atmos. Chem. Phys., vol. 19, No. 1, pp. 349-362, Jan. 2019.
R. S. Gao et al., "Computer-controlled Teflon flow control valve," Rev. Sci. Instrum., vol. 70, No. 12, p. 4732, 1999.
R. S. Gao, K. H. Rosenlof, D. W. Fahey, P. O. Wennberg, E. J. Hintsa, and T. F. Hanisco, "OH in the tropical upper troposphere and its relationships to solar radiation and reactive nitrogen," J. Atmos. Chem., vol. 71, No. 1, pp. 55-64, Mar. 2014.
J. M. Hoell, G. L. Gregory, and D. S. McDougal, "Airborne intercomparison of nitric oxide measurement techniques," J. Geophys. Res., vol. 92, No. D2, pp. 1995-2008, 1987.

M.-H. Hui and S. A. Rice, "Comment on 'Decay fluorescence from single vibronic levels of SO2,'" Chem. Phys. Lett., vol. 20, No. 5, pp. 411-412, Jul. 1973.
D. A. V Kliner, B. C. Daube, J. D. Burley, and S. C. Wofsy, "Laboratory investigation of the catalytic reduction technique for measurement of atmospheric NO y," J. Geophys. Res. Atmos., vol. 102, No. D9, pp. 10759-10776, May 1997.
A. R. Koss et al., "Non-methane organic gas emissions from biomass burning: identification, quantification, and emission factors from PTR-ToF during the FIREX 2016 laboratory experiment," Atmos. Chem. Phys., vol. 18, No. 5, pp. 3299-3319, Mar. 2018.
T. B. Ryerson et al., "Design and initial characterization of an inlet for gas-phase NO y measurements from aircraft," J. Geophys. Res. Atmos., vol. 104, No. D5, pp. 5483-5492, Mar. 1999.
J. L. Laughner and R. C. Cohen, "Direct observation of changing NO x lifetime in North American cities," Science (80-. )., vol. 366, No. 6466, pp. 723-727, Nov. 2019.
J. Luque and D. R. Crosley, "Radiative and predissociative rates for NO A 2Σ+v'=0-5 and D 2Σ+v'=0-3," J. Chem. Phys., vol. 112, No. 21, pp. 9411-9416, Jun. 2000.
C. Mitscherling, J. Lauenstein, C. Maul, A. A. Veselov, O. S. Vasyutinskii, and K.-H. Gericke, "Non-invasive and isotope-selective laser-induced fluorescence spectroscopy of nitric oxide in exhaled air," J. Breath Res., vol. 1, No. 2, p. 026003, Dec. 2007.
J. E. Murphy, B. A. Bushaw, and R. J. Miller, "Doppler-Free Two-Photon Fluorescence Excitation Spectroscopy of the A ← X(1,0) Band of Nitric Oxide: Fine Structure Parameter for the (3sσ)A2Σ+(v=1) Rydberg State of 14N16O," J. Mol. Spectrosc., vol. 159, No. 1, pp. 217-229, May 1993.
J. B. Nee, C. Y. Juan, J. Y. Hsu, J. C. Yang, and W. J. Chen, "The electronic quenching rates of NO(A, v'=0-2)," Chem. Phys., vol. 300, No. 1-3, pp. 85-92, May 2004.
I. B. Pollack, B. M. Lerner, and T. B. Ryerson, "Evaluation of ultraviolet light-emitting diodes for detection of atmospheric NO2 by photolysis—chemiluminescence," J Atmos. Chem., vol. 65, No. 2-3, pp. 111-125, Apr. 2010.
B. A. Ridley and L. C. Howlett, "An instrument for nitric oxide measurements in the stratosphere," Rev. Sci. Instrum., vol. 45, p. 742, 1974.
A. W. Rollins et al., "A laser-induced fluorescence instrument for aircraft measurements of sulfur dioxide in the upper troposphere and lower stratosphere," Atmos. Meas. Tech., vol. 9, No. 9, pp. 4601-4613, Sep. 2016.
H. Scheingraber and C. R. Vidal, "Fluorescence spectroscopy and Franck-Condon-factor measurements of low-lying NO Rydberg states," J. Opt. Soc. Am. B, vol. 2, No. 2, p. 343, Feb. 1985.
R. F. Silvern et al., "Observed NO/NO 2 Ratios in the Upper Troposphere Imply Errors in NO—NO 2-O 3 Cycling Kinetics or an Unaccounted NO x Reservoir," Geophys. Res. Lett., vol. 45, No. 9, pp. 4466-4474, May 2018.
H. B. Singh et al., "Reactive nitrogen and ozone over the western Pacific: Distribution, partitioning, and sources," J. Geophys. Res. Atmos., vol. 101, No. D1, pp. 1793-1808, Jan. 1996.
S. Solomon, "Stratospheric ozone depletion: A review of concepts and history," Rev. Geophys., vol. 37, No. 3, pp. 275-316, 1999.
S. Tilmes et al., "Effects of Different Stratospheric SO2 Injection Altitudes on Stratospheric Chemistry and Dynamics," J. Geophys. Res. Atmos., vol. 123, No. 9, pp. 4654-4673, 2018.
P. O. Wennberg et al., "Aircraft-borne, laser-induced fluorescence instrument for the in situ detection of hydroxyl and hydroperoxyl radicals," Rev. Sci. Instrum., vol. 65, No. 6, pp. 1858-1876, 1994.
C. M. Western, "PGOPHER: A program for simulating rotational, vibrational and electronic spectra," J. Quant. Spectrosc. Radiat. Transf., vol. 186, pp. 221-242, Jan. 2017.
Y. Zhao et al., "Inter-model comparison of global hydroxyl radical (OH) distributions and their impact on atmospheric methane over the 2000-2016 period," Atmos. Chem. Phys., vol. 19, No. 21, pp. 13701-13723, Nov. 2019.

* cited by examiner

METHODS AND APPARATUS FOR DETECTING NITRIC OXIDE

STATEMENT REGARDING FEDERAL RIGHTS

The invention described herein was made with support from the National Oceanic and Atmospheric Administration (NOAA) of the United States Department of Commerce. The United States Government has certain rights in the invention.

FIELD OF THE INVENTION

The present invention relates generally to methods and apparatus for trace gas detection using laser induced fluorescence (LIF).

BACKGROUND OF THE INVENTION

Nitric oxide (NO) is important to radical chemistry in Earth's atmosphere. In the troposphere the catalytic reaction of NO with the hydroperoxy and organic peroxy radicals

$$NO+RO_2/HO_2 \rightarrow NO_2+RO/HO \qquad (1)$$

is frequently the rate-limiting step for the production of tropospheric ozone ($O_3$), and causes the buildup of $O_3$ from anthropogenic emissions of NO. Oxidation of NO also results in the formation of nitric acid, and consequently nitrate aerosols and nitrogen deposition. Current research in atmospheric science seek to understand radical chemistry cycling in low NO regimes. The ability to measure atmospheric NO at very low mixing ratios and with low uncertainty will be crucial to address questions in atmospheric chemistry research and in other fields of research for the foreseeable future. For example, measurement of NO in exhaled human breath is also an important diagnostic of various medical conditions including asthma.

Research associated with direct detection of atmospheric NO has relied on the chemiluminescence (CL) detection technique. This technique has several drawbacks. An alternative technique that has been explored previously for NO measurement is laser-induced fluorescence (LIF).

Previously described LIF systems for the detection of NO are impractical for many applications. They rely on large, inefficient, cumbersome laser systems which are very sensitive to the working environment. Further, the demonstrated detection limits have not been a clear improvement compared with the CL instruments due to limitations in laser power and linewidth.

Accordingly, there is a need for methods and apparatus for the measurement of NO at low signal levels and for distinguishing the NO isotopologues. There is also a need for a NO measurement apparatus having laser linewidth that is sufficiently narrow to resolve the Doppler broadened NO spectrum at room temperature, laser repetition rate capable of enabling single-photon counting of the fluorescence signal, and having size, weight and environmental robustness allowing for integration onto airborne platforms.

SUMMARY OF THE INVENTION

Embodiments of the present invention relate to methods and apparatus for detecting NO at signal levels of about single parts per trillion mixing ratios of NO and for distinguishing the NO isotopologues. More particularly, embodiments of the present invention relate to methods and apparatus for a single photon LIF sensor that pumps the $A^2\Sigma$ $(v'=1) \leftarrow X^2\Pi(v''=0)$ vibronic transition near 215 nm and observes the resulting red shifted fluorescence from about 255 nm to about 267 nm. Embodiments of the present system uses a NO-LIF measurement fiber-amplified laser system capable of: generating laser linewidth that is sufficiently narrow to resolve the Doppler broadened NO spectrum at room temperature and thereby achieve high signal levels and distinguish the NO isotopologues; generating laser repetition rate sufficient to enable single-photon counting of the fluorescence signal; and having size, weight and environmental robustness allowing for integration onto airborne platforms.

Accordingly, embodiments of the present invention relate to an apparatus for detecting NO in a gas sample, including a first laser source providing a pulsed first laser beam having a first wavelength; a fiber optic amplifier system to amplify the pulsed first laser beam, wherein the fiber optic amplifier system maintains spectral purity of the pulsed first laser beam; a frequency conversion system to convert the pulsed first laser beam to a fifth harmonic pulsed first laser beam having a second wavelength; an optical cell for receiving the gas sample, wherein a longitudinal axis of the optical cell intersect orthogonally with the gas sample flow through the optical cell, wherein the fifth harmonic pulsed first laser beam propagates along the longitudinal axis of the optical cell and intersects the gas sample flow at a first location in the optical cell; a second laser source for propagating a second laser beam through the optical cell, wherein the second laser beam intersects orthogonally with the gas sample flow in the optical cell at the first location, wherein the second laser beam photolyzes nitrogen dioxide ($NO_2$) in the gas sample to NO at the first location, wherein the pulsed first laser beam intersecting the gas sample at the first location excite the NO in the gas sample to emit a fluorescence signal; and a first photodetector configured to detect the fluorescence signal emitted at the first location in the optical cell. More particularly, the second wavelength of the fifth harmonic pulsed first laser beam is about 215 nm. In one aspect of the present invention, the first wavelength of the pulsed first laser beam from the first laser source is about 1075 nm.

Some embodiments of the present invention further include a collimator operatively coupled to receive the pulsed first laser beam from the first laser source, wherein the collimator reduces spatial cross section of the pulsed first laser beam to a predetermined diameter; a first optical lens having an optical axis perpendicular to the optical axis of the pulsed first laser beam, wherein the first optical lens is positioned on a first side of the optical cell to focus the fluorescence signal to the first photodetector; a concave mirror for collecting the fluorescence signal, wherein an optical axis of the concave mirror is perpendicular to the optical axis of the pulsed first laser beam, wherein the optical axis of the concave mirror aligns with the optical axis of the first optical lens, wherein the concave mirror is positioned on a second side of the optical cell; a second optical lens having an optical axis in alignment with the optical axis of the first optical lens; and a bandpass filter positioned between the first and second optical lens, wherein the bandpass filter is adapted to block the pulsed first laser beam.

In another embodiments of the present invention, the frequency conversion system further includes a first optical waveplate to alter polarization state of the pulsed first laser beam; a first non-linear optical crystal positioned to receive the pulsed first laser beam from the first optical waveplate, wherein the first non-linear optical crystal converts the received pulsed first laser beam having the first wavelength to a second harmonic pulsed first laser beam having a third wavelength; a second non-linear optical crystal positioned to receive the second harmonic pulsed first laser beam from the first non-linear optical crystal, wherein the second non-linear optical crystal converts the received pulsed first laser beam having the second wavelength to a third harmonic pulsed first laser beam having a fourth wavelength; a second optical waveplate positioned to receive the third harmonic pulsed first laser beam from the second non-linear optical crystal, wherein the second optical waveplate rotates residual laser pulses received from the first optical waveplate to align with an axis of the third harmonic pulsed first laser beam received from the second non-linear optical crystal; a third non-linear optical crystal to provide the fifth harmonic generation pulsed first laser beam having the second wavelength; and an optical lens positioned between the second optical waveplate and the third non-linear optical crystal to focus the pulsed first laser beam exiting the second optical waveplate into the third non-linear optical crystal.

Other embodiments of the present invention further include a prism to separate the fifth harmonic pulsed first laser beam received from the frequency conversion system from residual laser pulses; a plurality of first dielectric mirrors for steering the separated fifth harmonic pulsed first laser beam exiting the prism for a single pass through the optical cell, wherein the pulsed first laser beam propagating through the optical cell intersect orthogonally with the gas sample flow in the optical cell; a plurality of second dielectric mirrors for steering the pulsed first laser beam exiting the optical cell, wherein the at least one second dielectric mirror splits the pulsed first laser beam into first and second portions at a predefined power ratio, wherein the optical cell is disposed between the at least one of the plurality of first dielectric mirrors and the at least one of the plurality of second dielectric mirrors; a reference fluorescence cell for receiving a reference gas sample, wherein a longitudinal axis of the reference fluorescence cell intersect orthogonally with the reference gas sample flow in the reference fluorescence cell, wherein a longitudinal axis of the reference fluorescence cell is in alignment with the optical axis of the second portion of the pulsed first laser beam propagating through the optical cell; a second photodetector for detecting fluorescence light exiting the reference fluorescence cell; a gas sampling system coupled to the optical cell and the reference fluorescence cell, wherein the gas sampling system maintains a predetermined mass flow rate of the gas sample inside the optical cell, wherein the gas sampling system maintains a predetermined mass flow rate of the reference gas sample inside the reference fluorescence cell; and a controller electrically coupled with the laser source and the first photon detector, wherein the controller controls timing of the pulsed first laser beam, wherein the controller controls photon detection gating of the first photodetector.

In one aspect of the present invention, the first non-linear optical crystal is selected from a group comprising potassium titanyl phosphate, periodically poled lithium niobate, or a combination comprising at least one of the foregoing; the second non-linear optical crystal is selected from a group comprising lithium triborate, periodically poled lithium niobate, or a combination comprising at least one of the foregoing; and the third non-linear optical crystal is a beta barium borate crystal.

Another embodiment of the present invention relates to an apparatus for detecting NO in a gas sample, including a first laser source providing a pulsed first laser beam having a first wavelength; a collimator to reduce spatial cross section of the pulsed first laser beam to a predetermined diameter, wherein the collimator is operatively coupled to receive the pulsed first laser beam from the first laser source; a first optical waveplate operatively coupled to receive the pulsed first laser beam from the collimator, wherein the first optical waveplate alters polarization state of the pulsed first laser beam received from the collimator; a first non-linear optical crystal positioned to convert the pulsed first laser beam having an altered polarization state to a second harmonic pulsed first laser beam having a second wavelength, wherein the second wavelength is about one-half of the first wavelength; a second non-linear optical crystal positioned to convert the second harmonic pulsed first laser beam having the second wavelength to a third harmonic pulsed first laser beam having a third wavelength, wherein the third wavelength is about one-third of the second wavelength; a third non-linear optical crystal positioned to convert the third harmonic pulsed first laser beam to a fifth harmonic generation pulsed first laser beam having a wavelength of about 215 nm; a prism to separate the fifth harmonic pulsed first laser beam received from the frequency conversion system from residual laser pulses; an optical cell for receiving the gas sample, wherein a longitudinal axis of the optical cell intersect orthogonally with the gas sample flow in the optical cell at a first location, wherein the fifth harmonic pulsed first laser beam propagates through the optical cell, wherein a longitudinal axis of the optical cell is in alignment with the optical axis of the fifth harmonic pulsed first laser beam propagating through the optical cell; a second laser source for propagating a second laser beam through the optical cell, wherein the second laser beam intersects orthogonally with the gas sample flow in the optical cell, wherein the pulsed second laser beam photolyzes nitrogen dioxide ($NO_2$) in the gas sample to NO at the first location, wherein the pulsed first laser beam passing through the optical cell intersect orthogonally with the gas sample flow in the optical cell; a first optical lens having an optical axis perpendicular to the optical axis of the pulsed first laser beam, wherein the first optical lens is positioned on a first side of the optical cell; a concave mirror for collecting a fluorescence signal, wherein an optical axis of the concave mirror is perpendicular to the optical axis of the pulsed first laser beam, wherein the optical axis of the concave mirror aligns with the optical axis of the optical lens, wherein the concave mirror is positioned on a second side of the optical cell; a first photodetector configured to detect a first fluorescence light, wherein the first photodetector is positioned in optical alignment with the concave mirror and the first optical lens; a reference fluorescence cell for receiving a reference gas sample, wherein a longitudinal axis of the reference fluorescence cell intersect orthogonally with the reference gas sample flowing through the reference fluorescence cell, wherein a longitudinal axis of the reference fluorescence cell is in alignment with the optical axis of the second portion of the pulsed first laser beam propagating through the optical cell; and a second photodetector for detecting a second fluorescence light exiting the reference fluorescence cell. In one aspect of the present invention, the pulsed first laser beam from the laser source has a wavelength of about 1075 nm.

In one embodiment of the present invention, the frequency conversion system further includes a second optical waveplate positioned to receive the third harmonic pulsed first laser beam from the second non-linear optical crystal, wherein the third harmonic pulsed first laser beam comprises residual laser pulses from the first optical waveplate, wherein the second optical waveplate rotates the residual laser pulses from the first optical waveplate to align an axis of the residual laser pulses parallel to an axis of the third harmonic pulsed first laser beam received from the second non-linear optical crystal; and an optical lens positioned between the second optical waveplate and the third non-linear optical crystal to focus the pulsed first laser beam exiting the second optical waveplate into the third non-linear optical crystal.

Another embodiment of the present invention further includes a plurality of first dielectric mirrors for steering the separated fifth harmonic pulsed first laser beam exiting the prism for a single pass through the optical cell, wherein the pulsed first laser beam propagating through the optical cell intersect orthogonally with the gas sample flow in the optical cell; a plurality of second dielectric mirrors for steering the pulsed first laser beam exiting the optical cell, wherein the at least one second dielectric mirror splits the pulsed first laser beam into first and second portions at a predefined power ratio; a solar-blind power monitoring phototube for measuring the first portion of the pulsed first laser beam exiting the laser induced fluorescence cell, wherein the optical cell is disposed between the at least one of the plurality of the first dielectric mirror and the at least one of the plurality of the second dielectric mirrors; a second optical lens having an optical axis in alignment with the optical axis of the first optical lens; and a bandpass filter positioned between the first and second optical lens, wherein the bandpass filter is adapted to block the pulsed first laser beam; a gas sampling system coupled to the optical cell and the reference fluorescence cell, wherein the gas sampling system maintains a predetermined mass flow rate of the gas sample inside the optical cell, wherein the gas sampling system maintains a predetermined mass flow rate of the reference gas sample inside the reference fluorescence cell; and a controller electrically coupled with the laser source and the first photon detector, wherein the controller controls timing of the pulsed first laser beam, wherein the controller controls photon detection gating of the first photon detector.

Embodiments of the present invention also relate to a method for detecting NO in a gas sample, including generating an amplified pulsed first laser beam having a first wavelength and a second laser beam having a second wavelength; reducing spatial cross section of the pulsed first laser beam to a predetermined diameter; altering polarization state of the pulsed first laser beam; converting the pulsed first laser beam to a fifth harmonic pulsed first laser beam having a third wavelength; optically transmitting the fifth harmonic pulsed first laser beam having the third wavelength through the gas sample flowing orthogonally to an axis of the fifth harmonic pulsed first laser beam, wherein the fifth harmonic pulsed first laser beam intersect the gas sample at a first location, wherein the fifth harmonic pulsed first laser beam intersecting the gas sample excite the NO in the gas sample to emit a fluorescence light; optically transmitting the second laser beam having the second wavelength orthogonally through the gas sample flowing to photolyze nitrogen dioxide ($NO_2$) in the gas sample to NO, wherein the second laser beam intersect the gas sample at the first location; detecting the fluorescence light emitted from the first location; and analyzing the detected fluorescence light to detect the NO in the gas sample. More particularly, the wavelength of the fifth harmonic pulsed first laser beam is about 215 nm.

DETAILED DESCRIPTION

While the making and use of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention, and do not limit the scope of the present invention.

Figure 1:
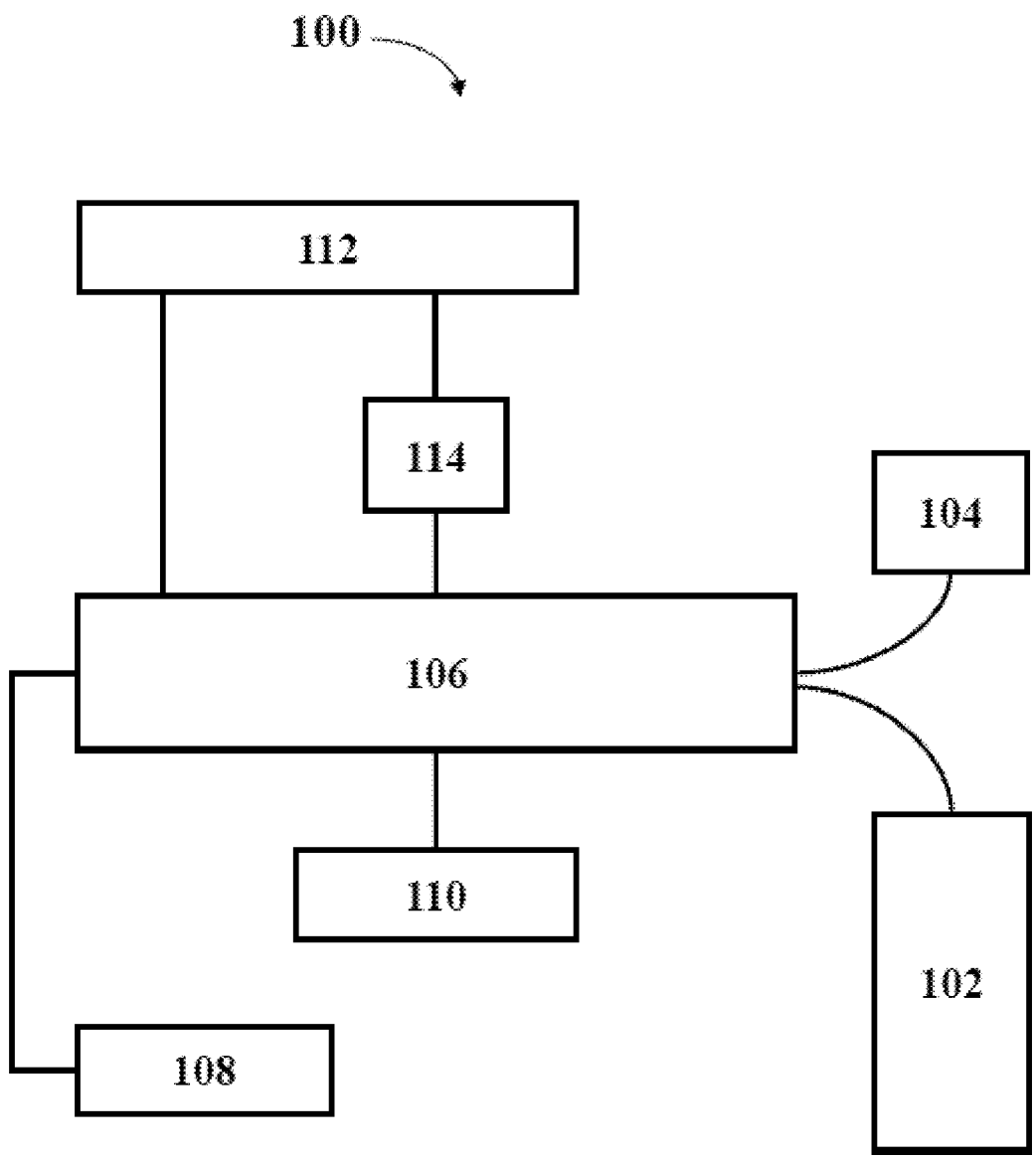
FIG. 1 illustrates an exemplary layout of a NO detection apparatus in accordance with an embodiment of the present invention.

Referring now to the drawings, and more particularly, to FIG. 1, there is shown an apparatus for the detection of NO in atmosphere, generally designated 100, which comprises embodiments of the present invention. NO detection apparatus 100 includes fiber laser system 102, second laser source 104, laser induced fluorescence (LIF) cell 106, reference fluorescence cell 108, gas sampling system 110, data collection and instrument control system 112, and photocathode detector 114.

Figure 2:
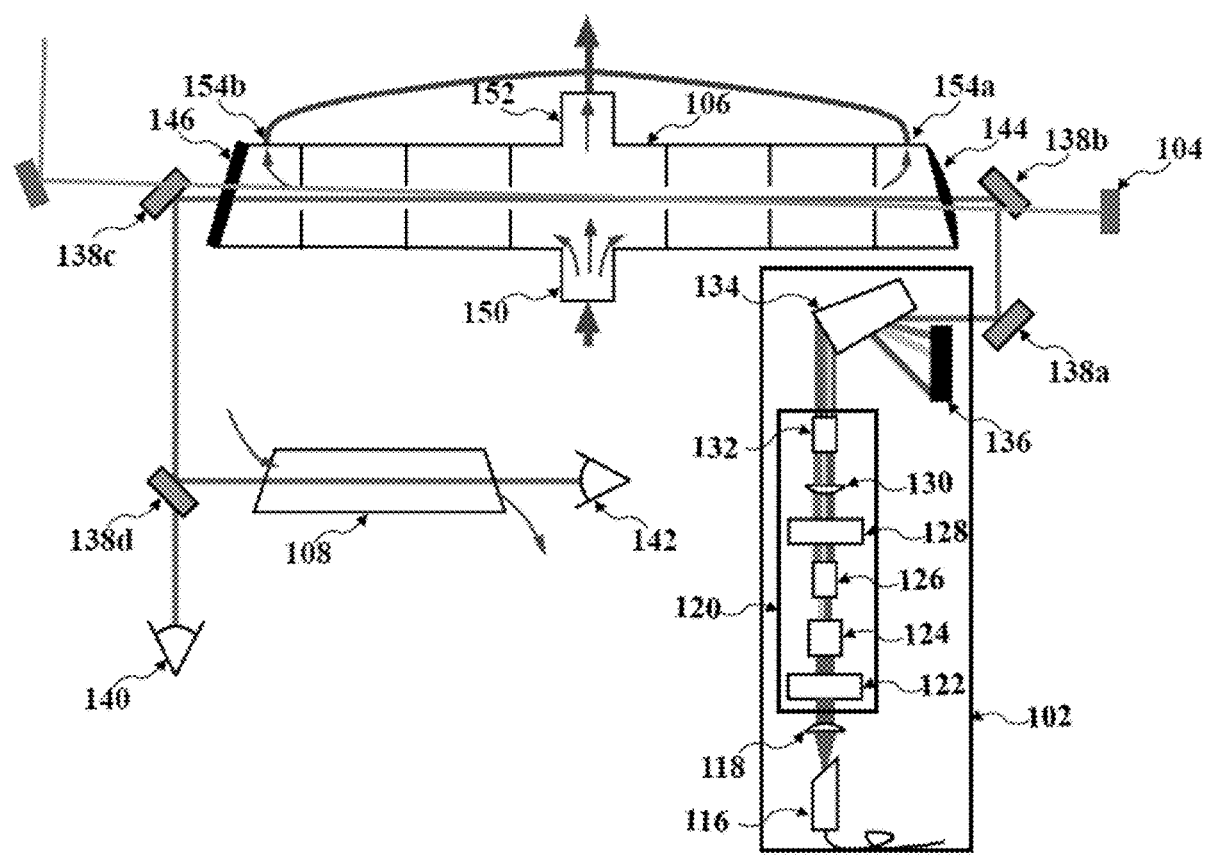
FIG. 2 illustrates an alternate view of an exemplary layout of a NO detection apparatus in accordance with an embodiment of the present invention.

FIG. 2 shows an exemplary layout of NO detection apparatus 100 illustrating components of fiber laser system 102, second laser source 104, LIF cell 106, reference fluorescence cell 108, dielectric mirrors 138a-d, solar-blind power monitoring phototube 140, and second phototube 142. Components of fiber laser system 102, as shown in FIG. 2, includes first laser source 116, collimating lens 118, frequency conversion system 120, prism 134, and optical beam block 136. Frequency conversion system 120 includes first optical waveplate 122, first non-linear optical crystal 124, second non-linear optical crystal 126, second optical waveplate 128, optical lens 130, and third non-linear optical crystal 132.

Laser source 116 provides a pulsed laser beam having a predetermined wavelength controlled by modulating the current to laser source 116. The pulsed laser beam is amplified using a fiber optic amplifier system and then collimated in collimator 118 to cause the spatial cross section of pulsed laser beam to have a predetermined diameter. The fiber optic amplifier system maintains spectral purity of the pulsed first laser beam. In one embodiment of the present invention, laser source 116 is a fiber-amplified laser system. The wavelength of the pulsed laser beam is controlled using a seed laser which may be a fiber-coupled distributed feedback laser (DFB) capable of providing up to 50 mW continuous wave optical power in a single-mode polarization-maintaining fiber. Exemplary seed laser for controlling the wavelength of the pulsed laser beam include a distributed bragg reflector laser (DBR), a tunable fiber-coupled diode laser, and the like. The DFB laser is capable of being tuned by modulating the current to obtain a laser having a wavelength in the range of from about 1074 nm to about 1076 nm with a nominal linewidth of about 10 MHz. The DFB output is chopped to obtain pulses of from about 2 ns to about 3 ns in duration with a 320 kHz repetition rate using a fiber-coupled electro-optic modulator with 10 GHz of switching bandwidth and an extinction ratio of 40 dB. In one embodiment of the present invention, laser pulses may be generated using an acousto-optic modulator. In another embodiment of the present invention, laser pulses may be generated by gain-switching of a fiber-coupled semiconductor optical amplifier instead of using the electro-optic modulator. About 40 pJ pulses are amplified in a multi-stage ytterbium-doped (Yb-doped) fiber amplifier to about 5 µJ, allowed to exit the fiber-amplifier system through an end-capped fiber, and then the beam is collimated to a diameter of about 350 µm. The resulting pulsed laser beam is allowed to transmit through a half-waveplate ($\lambda/2$) having a wavelength of about 1075 nm. In one embodiment of the present invention, the first fiber amplification stage is a regenerative amplifier that uses a narrow bandpass filter to achieve high gain with high spectral purity. This is advantageous in embodiments including Yb-doped fiber amplifier because Yb-doped fibers preferentially amplify light closer to 1030 nm while amplification of 1075 nm light is more difficult to achieve. Using a regenerative amplifier with a bandpass filter for selecting the 1075 nm light significantly reduces the amplified spontaneous emission output from the system while simultaneously improving the efficiency of the laser amplifier system.

Pulsed laser beam exiting collimating lens 118 passes through frequency conversion system 120 to obtain laser pulse having a predetermined wavelength. In one embodiment of the present invention, pulsed laser beam exiting collimating lens 118 passes through frequency conversion system 120 to convert long wavelength light to shorter wavelength light. The polarization state of the pulsed laser beam entering frequency conversion system 120 is altered by allowing the pulsed laser beam to pass through first optical waveplate 122. The pulsed laser beam exiting first optical waveplate 122 passes through a first non-linear optical crystal 124 to provide a second harmonic generation that is capable of converting the pulsed laser beam entering first non-linear optical crystal 124 to pulsed laser beam having a wavelength that is about one-half of the pulsed laser beam entering first non-linear optical crystal 124. In one embodiment of the present invention, first non-linear optical crystal 124 is a type-II phase matched potassium titanyl phosphate (KTP) crystal (3 mm×3 mm×10 mm) capable of generating a second harmonic at 537.5 nm. In another embodiment of the present invention, first non-linear optical crystal 124 is a periodically poles lithium niobate (PPLN) crystal. The pulsed laser beam exiting first non-linear optical crystal 124 passes through second non-linear optical crystal 126 to provide a third harmonic generation that is capable of converting the pulsed laser beam entering second non-linear optical crystal 126 to a wavelength that is about one-third of the pulsed laser beam entering second non-linear optical crystal 126. In alternate embodiments of the present invention, second non-linear optical crystal 126 mixes pulsed laser beam exiting first non-linear optical crystal 124 with residual laser pulses from waveplate 122 to generate a third harmonic laser pulse having a wavelength that is about one-third of the pulsed laser beam entering second non-linear optical crystal 126. In one embodiment of the present invention, second non-linear optical crystal 126 is a type-I phase matched lithium triborate (LBO) crystal (3 mm×3 mm×10 mm) capable of mixing pulsed laser beam having a wavelength of about 537.5 nm with residual laser pulses having a wavelength of about 1075 nm to produce a third harmonic pulsed laser beam having a wavelength at about 358.3 nm. In another embodiment of the present invention, second non-linear optical crystal 126 is a PPLN crystal.

Second optical waveplate 128 rotates residual laser pulses from first optical waveplate 122 to align its axis parallel to the axis of pulsed laser beam exiting second non-linear optical crystal 126. In one embodiment of the present invention, second optical waveplate 128 is a dual-wavelength waveplate ($\lambda/2$ @ 537.5 nm, $\lambda$ @ 358.3 nm) that is capable of rotating the residual second harmonic beam to be parallel with the third harmonic beam. Optical lens 130 focuses pulsed laser beam exiting second optical waveplate 128 into third non-linear optical crystal 132 to provide a fifth harmonic generation that is capable of converting the pulsed laser beam entering third non-linear optical crystal 132 to pulsed laser beam having a wavelength that is about one-fifth of the pulsed laser beam entering third non-linear optical crystal 132. In one embodiment of the present invention, optical lens 130 has a focal length of about 40 mm. In some embodiments of the present invention, third non-linear optical crystal 132 is a type-I phase matched beta barium borate (BBO) crystal (3 mm×5 mm×20 mm) capable of generating a fifth harmonic pulsed laser beam having a wavelength of about 215 nm. The pulsed laser beam pass through KTP, LBO and BBO crystals to produce the fifth harmonic pulsed laser beam having a wavelength of about 215 nm with a yield of about 1%. In alternate embodiments of the invention, PPLN crystals could be used to produce the second and third harmonics, which could then be combined with a BBO crystal to produce the fifth harmonic pulsed laser beam having a wavelength of about 215 nm.

Prism 134 separates residual laser pulses, including residual first and third harmonics, from the fifth harmonic pulsed laser beam exiting third non-linear optical crystal 132 of frequency conversion system 120. Residual laser pulses separated from the fifth harmonic pulsed laser beam exiting third non-linear optical crystal 132 are absorbed by optical beam block 136. The separated fifth harmonic pulsed laser beam exiting prism 134 is steered by dielectric mirrors 138a-b for a single pass through LIF cell 106. In one embodiment of the present invention, prism 134 is a Pellin-Broca prism that is capable of separating the first, second, and third harmonics and all of the residual light from the 215 nm pulsed laser beam, directing the separated residual light to beam block 136 and allowing the 215 nm pulsed laser beam to be steered by dielectric mirrors 138a-b into the LIF cell 106. In some embodiments of the present invention, laser source 116, waveplates 122 and 128, optical lens 130, prism 134 and beam block 136 are mounted on a 40 cm×55 cm×1.5 cm carbon fiber plate with stainless-steel inserts. In some embodiments of the present invention, non-linear crystals 124, 126 and 132 are mounted on a 9.5 mm thick temperature stabilized aluminum plate. In some embodiments of the present invention, waveplates 122 and 128 and prism 134 are surrounded by optical black-anodized aluminum sheeting to reduce eye hazard and insulated with Nomex to keep the optics at a near-constant temperature during operation. In such embodiments, the 215 nm pulsed laser beam exit the enclosure through a small hole and is steered by dielectric mirrors 138*a*-*b* for a single pass through LIF cell 106. In one embodiment of the present invention, dielectric mirrors 138*a*-*b* are positioned on piezo-driven mounts for remote alignment.

Figure 3:
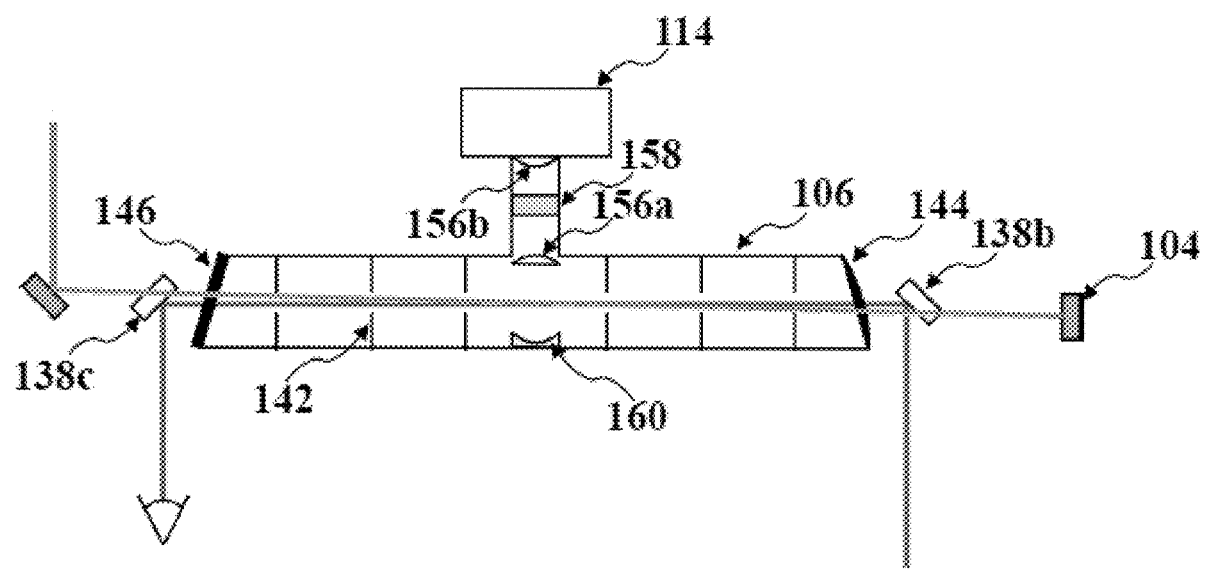
FIG. 3 illustrates an exemplary layout representing a LIF cell.

Referring now to FIG. 3, there is shown an alternate view of LIF cell 106. LIF cell 106 includes inlet lens 144, exit window 146, baffles 148, cell inlet valve 150, and cell outlet 152. The pulsed laser beam reflected from mirror 138*b* enters LIF cell 106 through inlet window 144 and exits LIF cell 106 through window 146, as further shown in FIG. 3. Window 144 is located at the proximal end of LIF cell 106 and is tilted to redirect reflections from the surface of window 144 away from the path of the pulsed laser beam entering LIF cell 106. In one embodiment of the present invention, window 144 is a V-type antireflection-coated fused silica window tilted at an angle of about 5 degrees to redirect reflections from the surface of window 144 away from the path of the laser beam entering LIF cell 106. LIF cell 106 further includes a plurality of baffles 148 located at a predetermined space from each other on the inner surface of LIF cell 106 such that the surface of baffles 148 is perpendicular to the longitudinal axis of LIF cell 106. Baffles 148 and the inner surface of LIF cell 106 are coated with light absorbing material capable of absorbing stray light. In some embodiments of the present invention, baffles 148 and inner surface of LIF cell 106 are coated with a combination of low reflectance black paint, black anodize, and molybdenum oxide treated aluminum. In other embodiments of the present invention, baffles 148 located in proximity to the center of LIF cell 106 are coated with an ultra-black carbon nanotube treatment. Each of baffles 148 includes an aperture located on its surface to allow the laser beam entering LIF cell 106 through inlet window 144 to pass unobstructed through the length of LIF cell 106 and exit through window 146. In one embodiment of the present invention, baffles 148 are circular baffles with about 2.5 mm to about 3.5 mm apertures.

LIF cell 106 includes sample cell inlet valve 150 and cell exit valve 152 located facing each other on the surface of LIF cell 106 such that a longitudinal axis traversing the centers of inlet valve 150 and exit valve 152 is perpendicular to the longitudinal axis traversing the center of LIF cell 106. Cell inlet valve 144 allows gas sample to enter LIF cell 106, which flows thorough apertures in baffles 148, fill the cavity of LIF cell 106 and exit LIF cell 106 via cell exit valve 152. In one embodiment of the present invention, LIF cell 106 includes secondary exit valves 154*a*-*b* located at the proximal and distal ends of LIF cell 106. The secondary exit valves 154*a*-*b* allow gas filling the cavity of LIF cell 106 to exit LIF cell 106 and combine with gas exiting LIF cell 106 via cell exit valve 152. The pulsed laser beam propagating through LIF cell 106 and gas flowing into LIF cell 106 via cell inlet valve 150 intersect orthogonally at about the center of LIF cell 106 and exits via window 146 located at the distal end of LIF cell 106. Window 146 is tilted to redirect reflections from the surface of window 146 away from the path of the laser beam exiting LIF cell 106. In one embodiment of the present invention, window 146 is a quartz window tilted at an angle of about 5 degrees to redirect reflections from the surface of window 146 away from the path of the laser beam exiting LIF cell 106.

Pulsed laser beam propagating through LIF cell 106 and intersecting orthogonally with gas flowing through LIF cell 106 results in fluorescence and scatter inside LIF cell 106. Pulsed laser beam propagating through LIF cell 106 substantially overlap with a second laser beam from a second laser source 104. Second laser beam from second laser source 104 propagates through LIF cell 106, intersects orthogonally with gas flowing in LIF cell 106 and photolyzes nitrogen dioxide ($NO_2$) in the gas to NO. Second laser beam from second laser source 104 intersects orthogonally with gas flowing in LIF cell 106 at substantially the same location where pulsed laser beam propagating through LIF cell 106 intersect orthogonally with gas flowing and where NO is measured inside LIF cell 106. The photolysis of $NO_2$ by second laser beam from second laser source 104 occurs prior to measuring NO. Instead of photolytically converting $NO_2$ into NO in a reaction vessel positioned prior to inlet valve 150, some embodiments of the present invention are capable of substantially overlapping the tunable laser having a wavelength from about 214 to about 216 nm with another light source capable of photolyzing $NO_2$ to sequentially photolyze $NO_2$ to NO immediately prior to the NO being measured by LIF. Exemplary photolysis light sources include a light emitting diode, laser, and the like, with each light source having a wavelength from about 250 nm to about 410 nm. Optical lens 156*a* located inside LIF cell 106 collects a portion of the fluorescence light and focusses the collected fluorescent light or photons through optical bandpass filter 158. In one embodiment of the present invention, optical lens 156*a*-*b* is a fused silica lens with numerical aperture of 0.5 and collects fluorescence light from the center of LIF cell 106. Optical mirror 160 is located on LIF cell 106 wall opposite to optical lens 156*a* and positioned facing optical lens 156*a* such that optical mirror 160 reflects scattered fluorescence light in LIF cell 106 to optical lens 156*a*. In some embodiments of the present invention, optical mirror 160 is a concave mirror located facing optical lens 156*a* to increase the collected fluorescence signal by about 50% by increasing the solid angle imaged onto photocathode detector 114. Bandpass filter 158 blocks or removes any scattered pulsed laser beam collected by optical lens 156*a* and allows filtered fluorescence light to pass through optical lens 156*b* before entering photocathode detector 114. In one embodiment of the present invention, bandpass filter 158 is a 260±8 nm bandpass filter. In other embodiments of the present invention, a second bandpass filter is located between optical lenses 156*a* and 156*b* to remove light scattered from second light source 104 used to photolyze $NO_2$.

Referring now to FIG. 2, the pulsed laser beam exiting LIF cell 106 is redirected by mirror 138*c* to mirror 138*d*. Mirror 138*d* splits the pulsed laser beam at a predefined power ratio allowing one portion of the split pulsed laser beam to enter solar-blind power monitoring phototube 140 and the other portion of the split pulsed laser beam to propagate through reference fluorescence cell 108 and into second phototube 142. In one embodiment of the present invention, mirror 138*d* splits the pulsed laser beam at a power ratio of about 10:90 with 10% of the power entering solar-blind power monitoring phototube 140 and 90% passing through a reference fluorescence cell 108.

Figure 4:
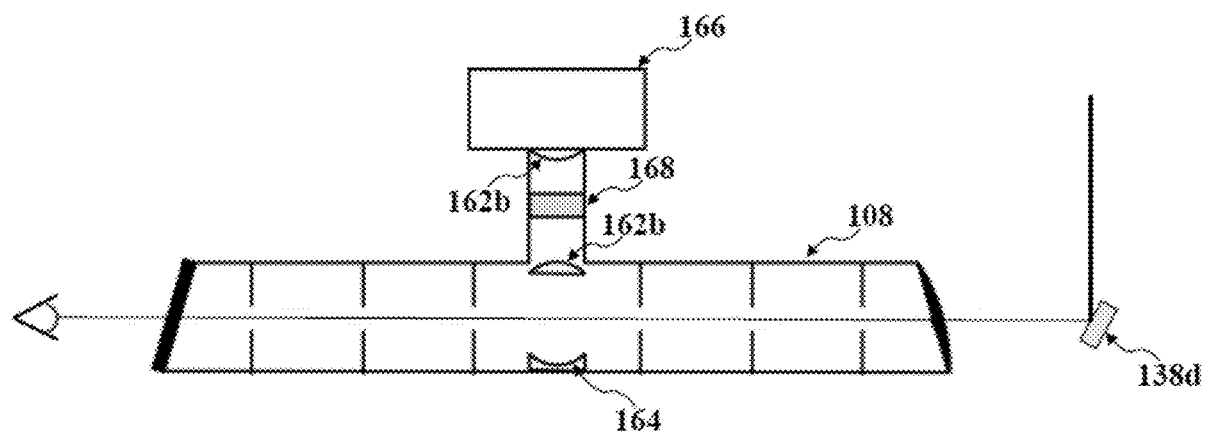
FIG. 4 illustrates an exemplary layout representing a reference fluorescence cell.

Reference fluorescence cell 108, as shown in FIG. 4, includes optical elements that are substantially similar to LIF cell 106. These include optical lenses 162*a*-*b* and a mirror 164 to collect and focus light onto a fluorescence detector 166, such as a photomultiplier tube (PMT), as well as bandpass filter 168 to select the fluorescence wavelength range. In one embodiment of the present invention, reference fluorescence cell 108 has a constant flow of about 500 ppbv NO at a rate of about 50 sccm. In embodiments of the present invention, the exhaust of reference fluorescence cell 108 is tied to the exhaust of LIF cell 106 such that both cells are at pressures of about 0.5 hPa during measurements. The pulsed laser beam propagating through reference fluorescence cell 108 and intersecting orthogonally with reference gas flowing through reference fluorescence cell 108 results in fluorescence and scatter inside reference fluorescence cell 108. Optical lens 162a located inside reference fluorescence cell 108 collects a portion of the fluorescence light and passes the collected fluorescent light or photons through bandpass filter 168. In one embodiment of the present invention, optical lens 162 is a fused silica lens with numerical aperture of about 0.5 and collects fluorescence light from the center of the cell. In some embodiments of the present invention, a concave mirror is located facing optical lens 162 to increase the collected fluorescence signal by about 50% by increasing the solid angle imaged onto photocathode detector 142. Bandpass filter 168 removes any scattered laser beam collected by optical lens 162 and allows filtered fluorescence light to enter photocathode detector 142. In one embodiment of the present invention, bandpass filter 168 is a 260±8 nm bandpass filter.

Figure 5:
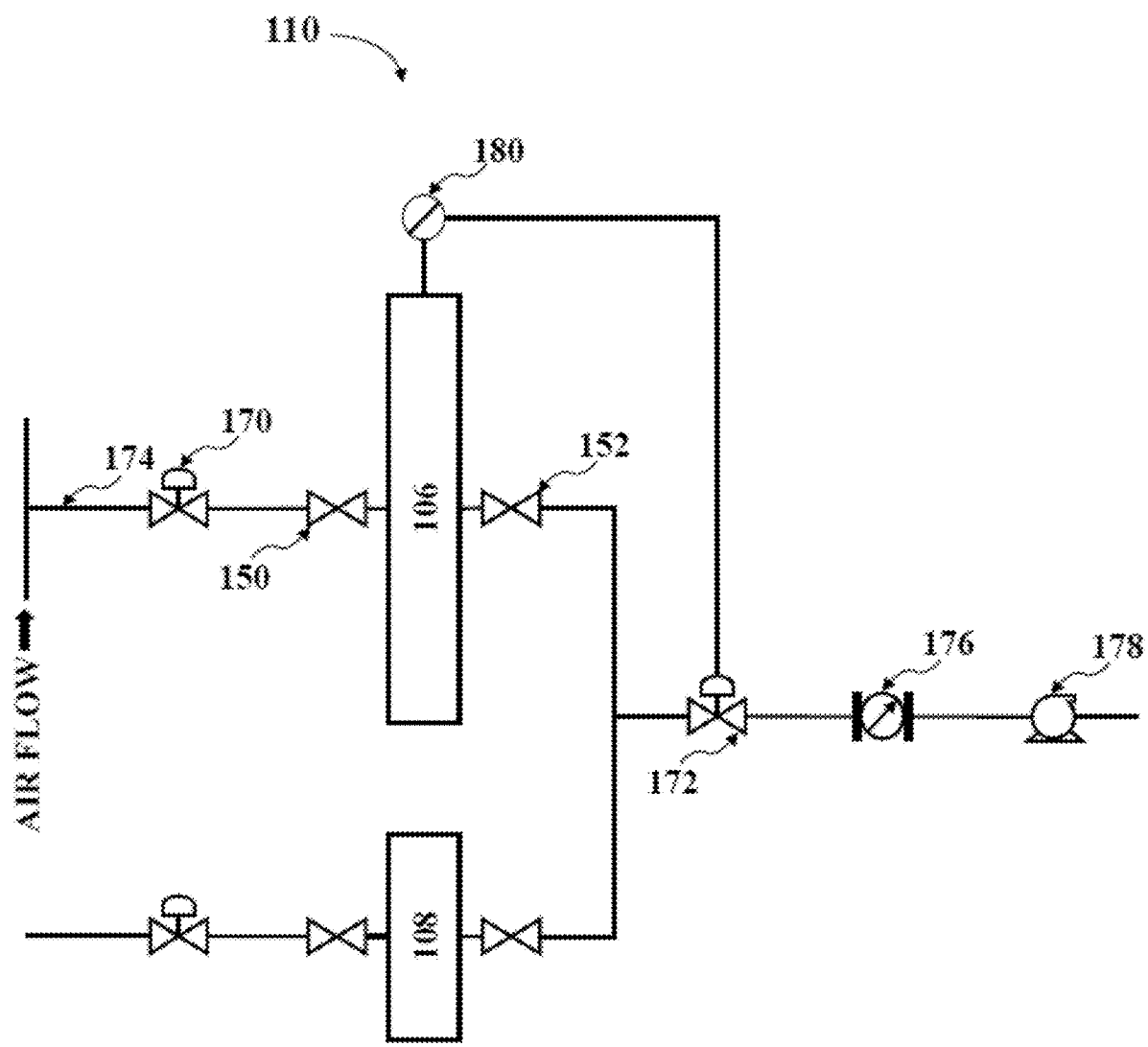
FIG. 5 illustrates exemplary layout representing a gas sampling system.

Referring now to FIG. 5, there is shown a gas sampling system 110 capable of maintaining constant mass flow and pressure inside LIF cell 106 during operation. In one embodiment of the present invention, gas sampling system 110 is capable of being mounted on an aircraft and capable of maintaining constant mass flow and pressure inside LIF cell 106 during operation of the aircraft at all altitude ranges. Gas sampling system 110 includes inlet valve 170 and exhaust valve 172 to control the mass flow of gas entering and exiting LIF cell 106. In one embodiment of the present invention, inlet valve 170 and exhaust valve 172 are butterfly valves. During typical operation of embodiments of the present invention, air is drawn through tube 174 having an inlet opening oriented perpendicular to the direction of airflow to eliminate super-micron particles from the sample gas. Exemplary materials used for tubing and fittings in gas sampling system 110 include teflon PFA (perfluoroalkoxy alkane), PEEK (polyetheretherketone) material, stainless steel, and the like. In at least one embodiment of the present invention, air is drawn through a 6.35 mm inner-diameter PFA tube having an inlet opening oriented perpendicular to the direction of airflow. A PFA tee in the sample line, located 5 cm from the inlet tip, is used to add zero and/or calibration gases to the inlet. Tubing and fittings are maintained at a temperature of about 45 degrees C.

Air sample entering gas sampling system 110 through tubing 174 passes through inlet valve 170 before entering LIF cell 106 through cell inlet valve 150. In one embodiment of the present invention, inlet valve 170 and sample exhaust valve 172 are butterfly valves constructed of PEEK material with a PFA vane. A substantial portion of gas sample flow exits through cell exit valve 152 located opposite cell inlet valve 150, and remaining portion of gas sample flow is drawn to the distal and proximal ends of LIF cell 106 to eliminate dead volume in the analysis region. Gas sample flow exiting cell exit valve 152 pass through sample exhaust valve 172 and a mass flow meter 176 to a scroll pump 178. In one embodiment of the present invention, scroll pump 178 provides a flow rate of about 160 liters per minute.

Inlet valve 170 and exhaust valve 172 control gas sample flow and pressure while minimizing pressure drop. In one embodiment, inlet valve 170 is servo controlled to a mass flow meter that measures the exhaust of the sample cell. Exhaust valve 172, which is located after the point where the sample and reference cell exhausts are tied together, is servo controlled using a pressure transducer 180 to measure the pressure immediately downstream of LIF cell 106. During typical operation of embodiments of the present invention in aircrafts, the pressure and flow are typically maintained to within a 1% range of their setpoints over the entire altitude range encountered. Flow through reference cell 108 is controlled using a pair of mass flow controllers to mix zero-air and gas from a NO standard gas cylinder.

Data collection and instrument control are performed by data collection and instrument control system 112 that incorporates a field-programmable gate array (FPGA) for controlling the timing of the laser and photon detection gating with a precision of 5 ns. The FPGA interfaces with digital inputs and outputs that can control the timing of laser pulse, timing of laser regenerative amplifier, and count the fluorescent photons detected by the PMT. Housekeeping data and instrument control, such as control of the laser wavelength, can also be controlled by data collection and instrument control system 112.

In an exemplary embodiment of the present invention, various elements of NO detection apparatus 100 are located in enclosures to maintain consistent temperatures during flight operations. In such embodiments of the present invention, LIF cell 106, reference fluorescence cell 108, gas sampling system 110, and data collection and instrument control system 112 are located in one enclosure, and fiber laser system 102 in a second enclosure. Exemplary dimensions of enclosure housing LIF cell 106, reference fluorescence cell 108, gas sampling system 110, and data collection and instrument control system 112 include 55 cm×43 cm×21 cm and of second enclosure housing fiber laser system 102 include 43 cm×43 cm×5 cm. In combination, these enclosures occupy about 26 cm of vertical rack space in a standard instrumentation rack and weigh about 31 kg. Typically, a vacuum scroll pump and a small calibration gas bottle are installed in the rack adjacent to the instrument and use another 21 cm of vertical rack space and weigh 19 kg.

Reference now to the specific examples which follows will provide a clearer understanding of systems in accordance with embodiments of the present invention. The examples should not be construed as a limitation upon the scope of the present invention.

Figure 6:
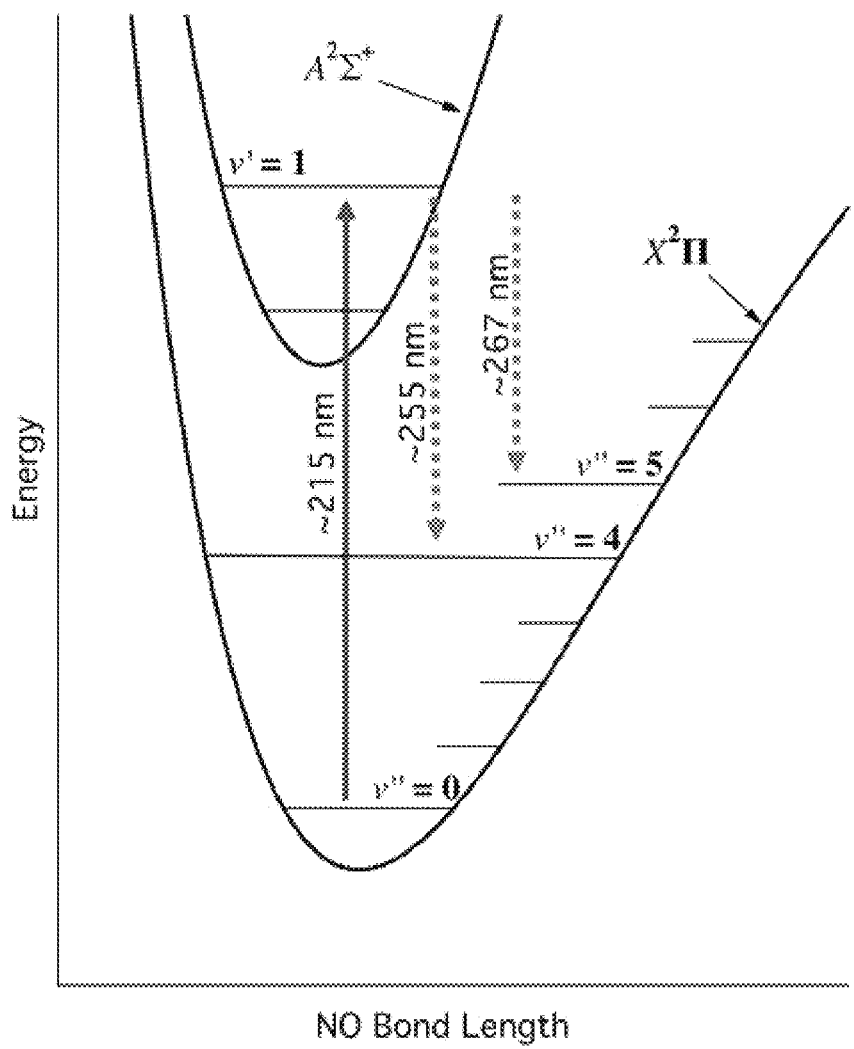
FIG. 6 illustrates an exemplary NO electronic potential energy surfaces and LIF scheme during a typical operation of embodiments of the present invention.
Figure 7:
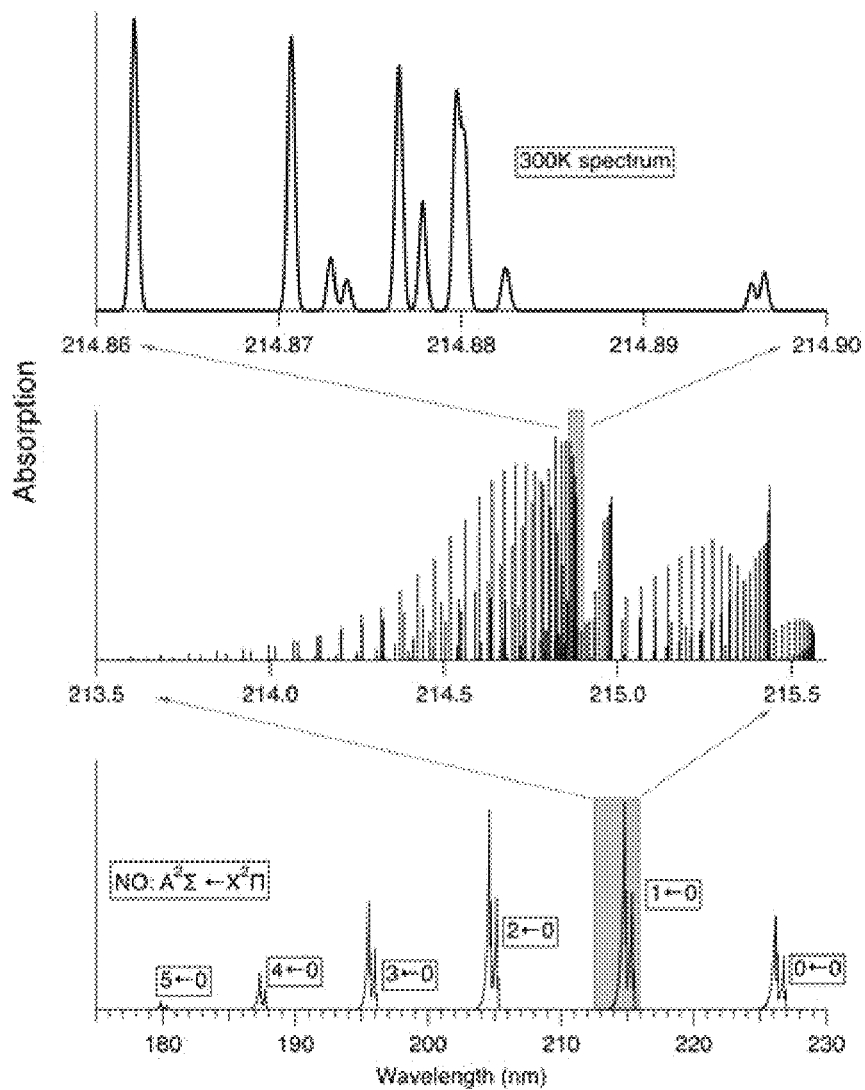
FIG. 7 illustrates an exemplary absorption spectrum of NO obtained during a typical operation of embodiments of the present invention.

Referring now to FIG. 6, there is shown exemplary NO electronic potential energy surfaces and LIF scheme during a typical operation of embodiments of the present invention. This includes pumping the $A^2\Sigma(v'=1) \leftarrow X^2\Pi(v''=0)$ transition near 215 nm, and observing the resulting red-shifted fluorescence from the $A^2\Sigma(v'=120\ 1) \leftarrow X^2\Pi(v''=4,5)$ transitions, as illustrated in the absorption spectrum of NO of FIG. 7. The tunable laser used in embodiments of the present invention pumps NO near 215 nm from the ground $X^2\Pi$ ($v''=0$) state into the $A^2\Sigma(v'=1)$ state. Using this excitation has multiple advantages over the $A^2\Sigma(v'=1) \leftarrow X^2\Pi(v''=0)$ excitation scheme pumping at 226 nm. First, the absorption cross section (a) for NO is about twice as high in the 1←0 transition compared to 0←0. Second, the additional vibrational energy provides a significant shift in the spectra of the various NO isotopologues, making them spectroscopically distinguishable. The origin of the $A^2\Sigma(v'=1) \leftarrow X^2\Pi(v''=0)$ transition for $^{14}N^{16}O$ is 46 cm$^{-1}$ and 70 cm$^{-1}$ higher in energy than those for the $^{15}N^{16}O$ and $^{14}N^{16}O$ isotopologues, respectively. Third, 215 nm can be produced using the fifth harmonic of a ytterbium-doped fiber amplifier system operating at 1075 nm, whereas 226 nm cannot currently be produced using such a system. In addition, excitation at 226 nm has the potential to produce spurious signal from fluorescence of $SO_2$ in air, while 215 nm is a minimum in the $SO_2$ absorption cross section, and the $SO_2$ fluorescence quantum yield here is less than 3%.

Figure 8:
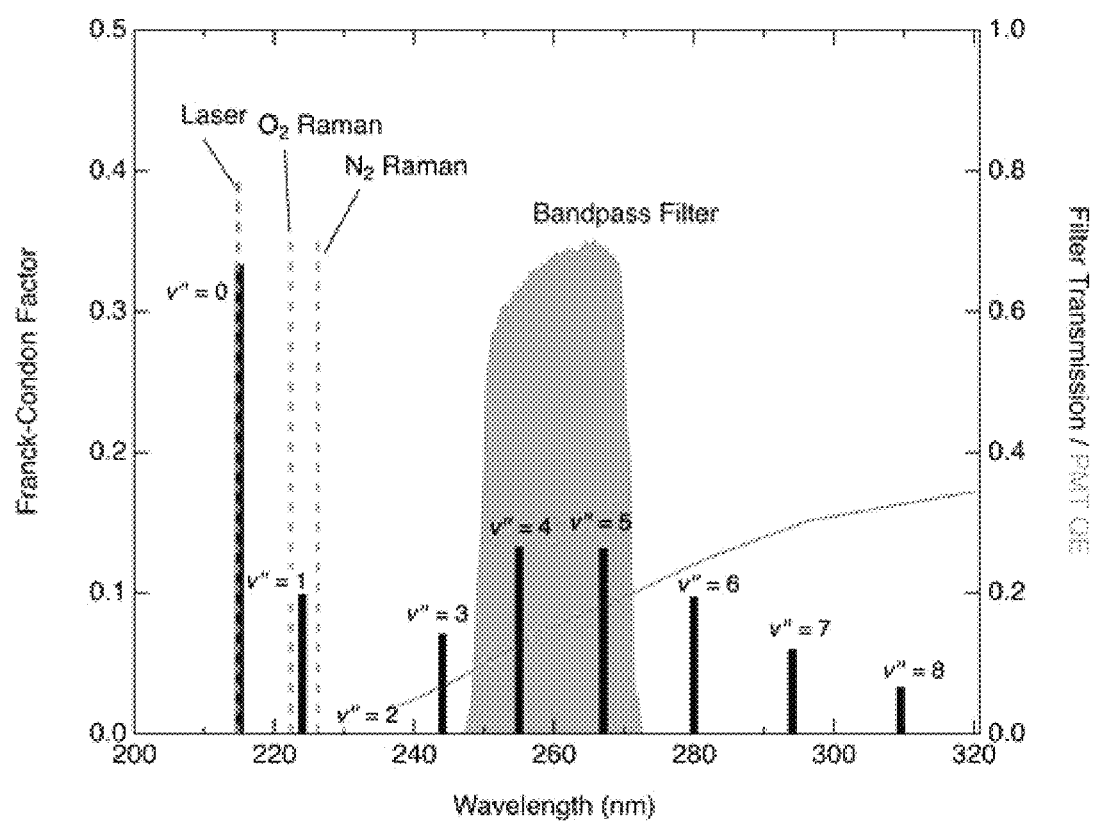
FIG. 8 illustrates an exemplary fluorescence emission spectrum based on the Franck-Condon factors.

FIG. 8 shows the expected fluorescence emission spectrum based on the Franck-Condon factors. Excluding the emission at $A^2\Sigma(v'=1) \leftarrow X^2\Pi(v''=0)$, which cannot be distinguished from Rayleigh scatter, fluorescence from the $A^2\Sigma(v'=1)$ state is expected to peak at v''=4 (255 nm) or v''=5 (267 nm) although it may be possible to collect significant signal from any of v''=3~8. Exemplary detection bandpass filter having optimal signal to noise ratio for NO detection include a filter centered at 260 nm with a full width of 16 nm (see FIG. 8). This detection bandpass filter has 63% transmission at the 1→4 transition (255 nm) and 69% transmission at 1→5 (267 nm) while completely rejecting laser Rayleigh and Raman scatter from $N_2$ and $O_2$. In embodiments of the present invention operating LIF cell 106 near 80 hPa, typical background using this filter is 10 counts $s^{-1}$ with 1 mW laser power. Of this background, about 1 count $s^{-1}$ is a dark count from the detector. Using a filter to additionally collect the 1→6 emission increases the signal by 4.5 counts $s^{-1}$ $mW^{-1}$ $pptv^{-1}$, but also increases the background to more than 350 counts $s^{-1}$ $mW^{-1}$ which would degrade the detection limit. It is expected that background levels would further increase at longer collection wavelengths while collecting the fluorescence from v''=3 at 244 nm would likely increase the signal without substantial increases in the background.

The precision with very low mixing ratios of NO in an embodiment of the present invention was measured in the laboratory to test for any zero artifacts and to determine the detection limit in at least one embodiment of the present invention. For these tests, the observed data were analyzed assuming that no artifact of any kind exists (i.e., the sampled NO mixing ratio is proportional to the difference between online and offline signals at all mixing ratios), and the instrument response as determined by additions of NO standards is linear down to zero concentration. It is typically found that flowing air directly from zero air cylinders into the instrument results in a measurement of 1-2 pptv NO. The observed NO was reduced to less than 0.2 pptv by flowing zero air through a potassium permanganate trap ($KMnO_4$).

Figure 9:
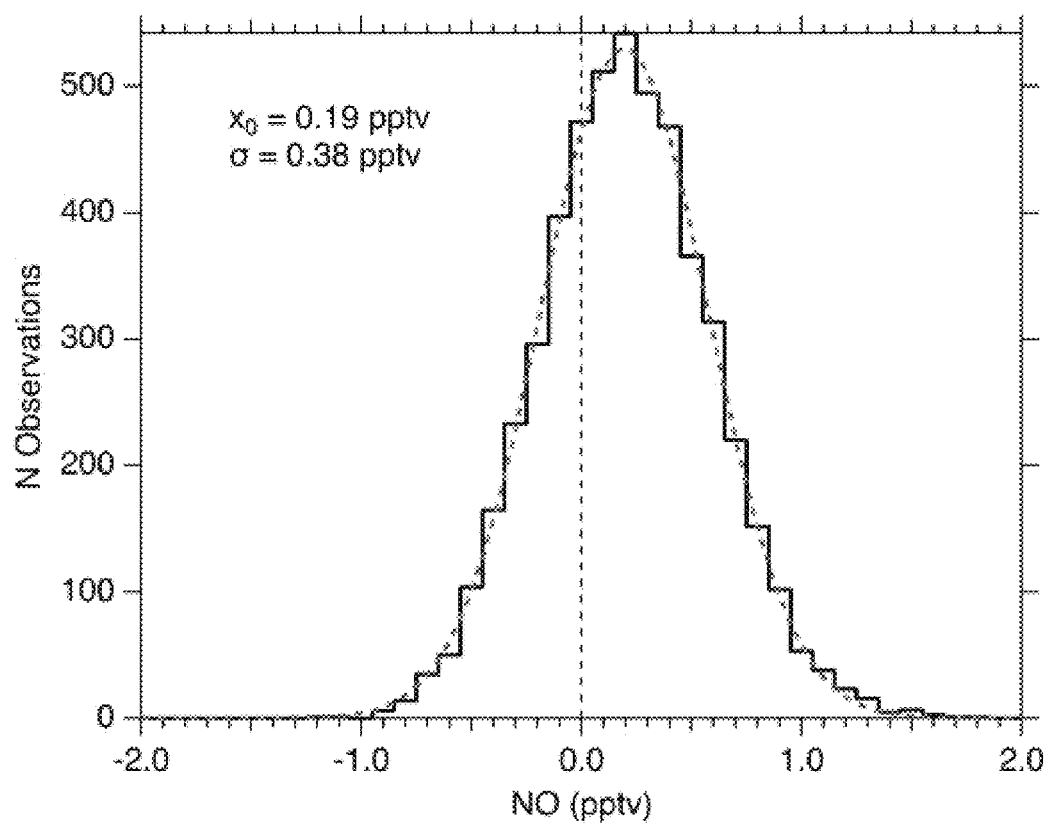
FIG. 9 illustrates an exemplary segment of ambient measurement data.

FIG. 9 shows the distribution of 1 Hz NO mixing ratios measured when sampling $KMnO_4$ scrubbed zero air for 1.4 hours in the laboratory. During this period, the mean NO measured was 0.19 pptv and the noise was normally distributed with a 2σ width of 0.76 pptv. For this period, the laser power was 0.9 mW, and the NO sensitivity was 10 counts $s^{-1}$ $mW^{-1}$. The average count rate was 12 counts $s^{-1}$, and the calculated background count rate is 10.3 counts $s^{-1}$. The width of the observed mixing ratio distribution is similar to an expected Poisson limited distribution of the photon counts (σ=(12 counts)/(10 counts $mW^{-1}$ $pptv^{-1}$×0.9 mW)=0.385 pptv). This suggests that no sources other than photon counting statistics contribute significantly to the precision near the detection limit. The calculated 2σ detection limit for a 1 second integration is therefore 0.97 pptv, and for ten seconds is 0.25 pptv. No evidence exists to suggest that the 0.19 pptv observed in the scrubbed zero air is due to anything other than NO remaining in that sample.

Figure 10:
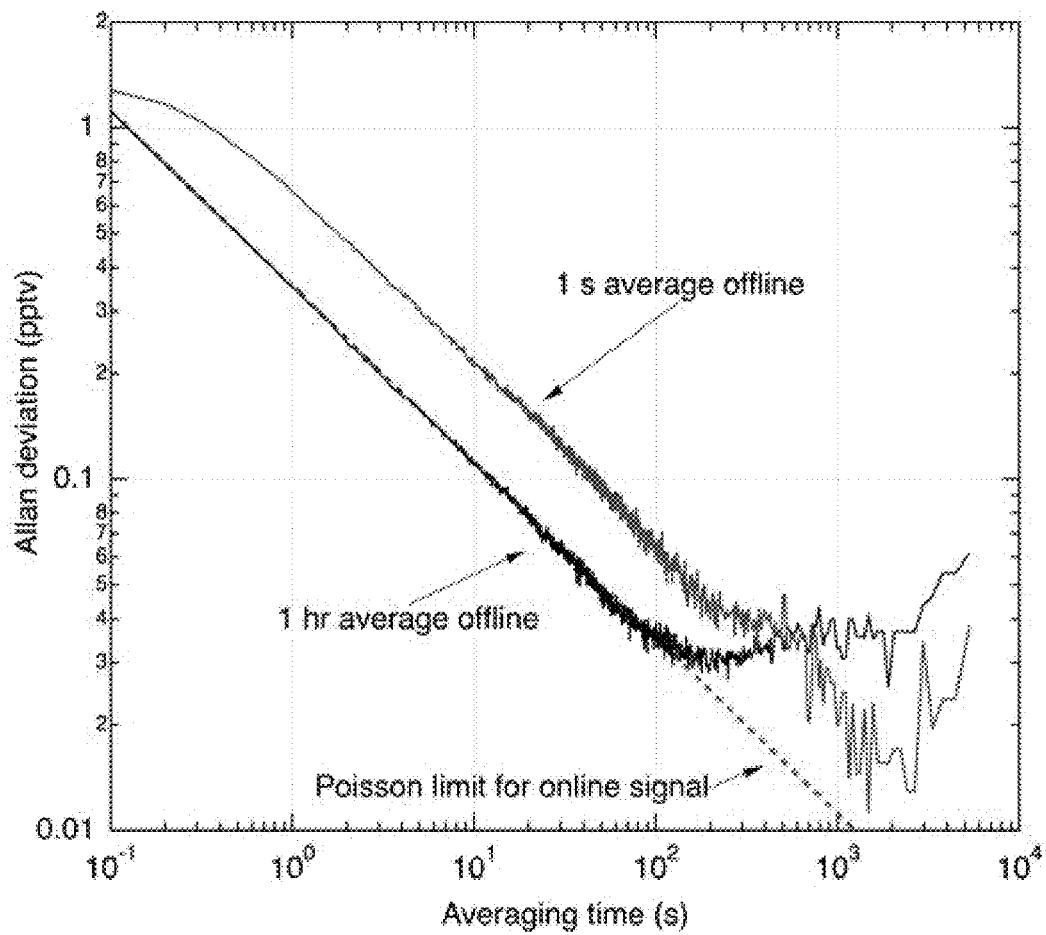
FIG. 10 illustrates an exemplary Allan deviation analysis from zero-air sampling.

FIG. 10 shows an Allan deviation analysis of the scrubbed zero-air sampling. During data reduction, sufficiently long averaging of the offline signal effectively eliminates the offline signal as a source of noise, while shorter averaging of the offline signal assures that any changes in offline signal are completely resolved. Two analyses are shown to illustrate this, one where a 1 hour average is used for the offline and another using a 1 second average offline. At integration times of less than 100 seconds, the analysis using a 1 hour average of the offline signal shows that the precision is limited only by the counting statistics associated with the online signal. Instabilities in the offline signal with time constant on the order of 100-1000 seconds leads to lower σ using the 1 s offline average for integrations exceeding by about 10 minutes.

Airborne operations using embodiments of the present invention provides a comparison of NO detection apparatus 100 with a CL instrument. The CL instrument was located at the front of the cabin, and sampled from a probe on the port side of the aircraft. NO detection apparatus 100 was located mid-cabin, with a probe extending from the starboard side of the aircraft. NO detection apparatus 100 shared the probe with four other instruments, each of which sampled about 2 slpm from the total flow of more than 20 slpm. Table 1 compares performance and physical characteristics for LIF and CL instruments.

TABLE 1

| | LIF | CL |
|---|---|---|
| Sensitivity | 10 CPS/pptv | 10 CPS/pptv |
| Background | 10 CPS | 800-1100 CPS |
| Detection Limit (1 Hz, 2σ) | 1 pptv | 6 pptv |
| Consumables | Trace NO for ref. cell | Pure $O_2$, cryogen |
| Power Consumption | 400 W | 2100 W |
| Mass | 50 kg | 150 kg |
| Quenching by 10,000 ppm $H_2O$ | 16% | 4% |

Figure 11:
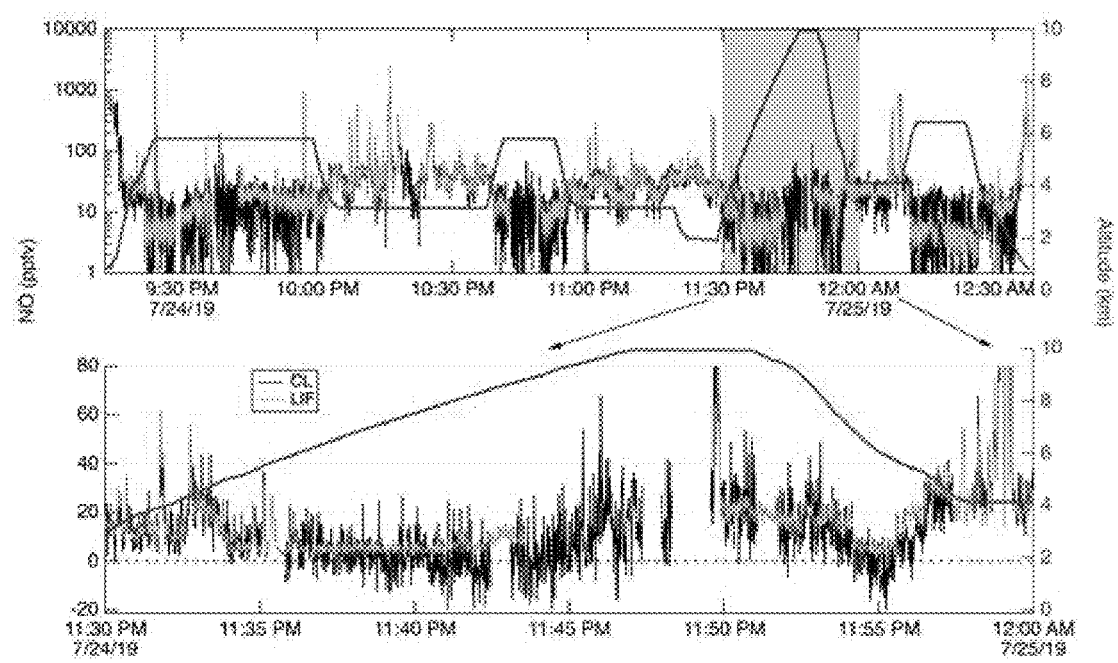
FIG. 11 illustrates an exemplary time series of the 1 Hz measurements from an airborne operation.
Figure 12:
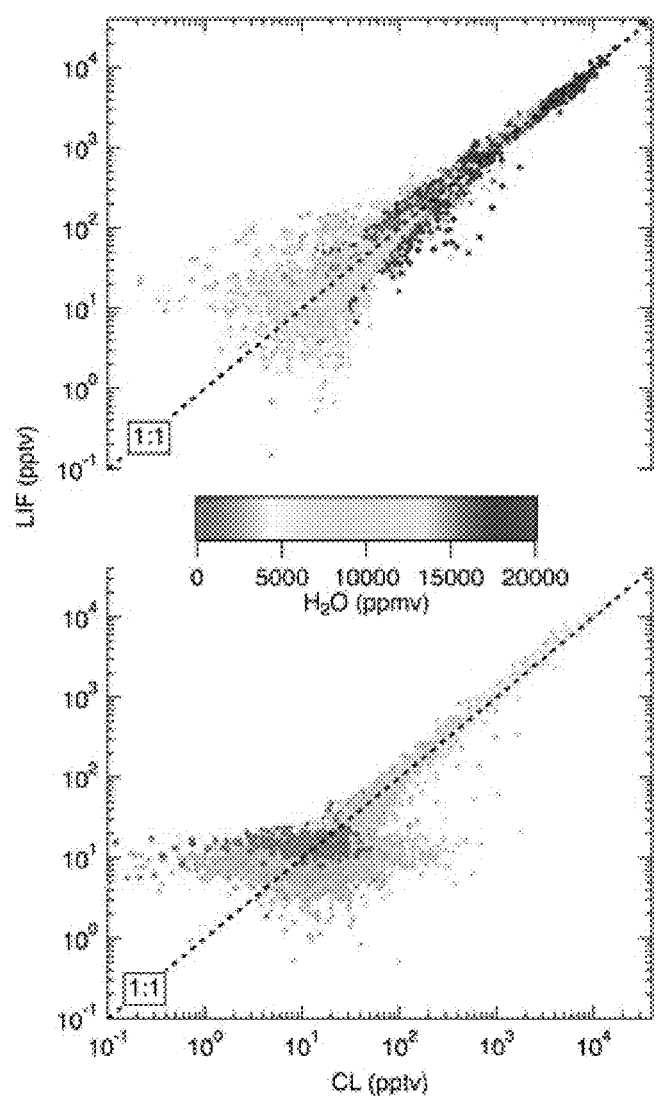
FIG. 12 illustrates an exemplary scatter plots of NO detection apparatus in accordance with the present invention and chemiluminescence data for two flights.

FIG. 11 shows a time series of the 1 Hz measurements from a 3.4-hour flight. Generally, agreement between an embodiment of NO detection apparatus 100 and CL instruments is observed and there is no evidence of detectable interferences in either instrument. Small differences were sometimes observed when leaving large plumes where the NO mixing ratio would decrease by more than one order of magnitude over the period of one second. These are believed to be due to a volume in the CL instrument sample line, which is designed to match the $NO_2$ photolysis volume in a paired channel. The lower noise of NO detection apparatus 100 is apparent primarily at mixing ratios lower than 10 pptv. FIG. 12 shows scatter plots of NO detection apparatus 100 and CL data for two flights. The top panel shows the comparison from a flight on a DC-8 aircraft, which sampled air throughout the California San Joaquin Valley, the Los Angeles Basin, and then transited at 12.5 km altitude to Boise, Id. The bottom panel shows measurements from the flight on a DC-8 aircraft, which sampled wildfire smoke while based in Boise, Ind. In both figures, the data are colored by the water vapor mixing ratio measured by trace gas analyzer to demonstrate that once the data are adjusted for the measured water vapor measurements, systematic differences due to differences in water vapor are not apparent. For all data shown in FIG. 12, the regression fit slope is 0.993, indicating that NO detection apparatus 100 measured NO was on average 0.7% lower than CL—a difference easily attributable to calibration uncertainties for either instrument.

Apparatus in accordance with embodiments of the present invention has several advantages over previous NO detection apparatus. Embodiments of the present invention selectively convert $NO_2$ to NO by utilizing light having a wavelength from about 250 nm to about 410 nm. In systems using chemiluminescence (CL) to measure $NO_2$, typically by detecting NO, a very high-power light source illuminating a reaction vessel of finite size is required to provide sufficient time with the $NO_2$ being exposed to the light to convert the $NO_2$ into NO. Instead of photolytically converting $NO_2$ into NO in an inlet/flow tube, embodiments of the present invention overlap spatially the laser beam used to measure NO by LIF with a focused laser or LED to photolyze the $NO_2$ into NO immediately prior to the NO being measured by LIF. This provides a method for measurement of $NO_2$ as well as NO without adding a volume with substantial residence time to the inlet of the instrument which can produce artifacts. This also reduces the light intensity required to photolyze the $NO_2$ because only a very small volume of gas, where the two beams overlap, needs to be photolyzed. Further, improvements in response time is achieved because a long residence time in the inlet/flow tube where $NO_2$ is normally photolyzed is not required, as shown in FIG. 3.

NO detection apparatus in accordance with embodiments of the present invention can be used for performing direct measurements of atmospheric NO using single-photon laser-induced fluorescence. The demonstrated detection limit for 10 s of integration is 0.3 pptv and appears to be the lowest detection limit at this time resolution that has been demonstrated for an airborne atmospheric NO sensor. Besides having excellent precision, embodiments of the present invention has significant practical advantages as compared to CL instruments. Consumables such as dry ice and pure oxygen are not required. CL instruments have background levels on the order of 10-100 pptv equivalent and the background typically decreases for a number of hours after instrument operation begins. CL background also increases significantly at high altitudes and latitudes due to the effect of cosmic rays on the large infrared-sensitive PMTs. At higher altitudes CL instrumental precision degrade relative to LIF as the aircraft climbs from about 2 km to about 10 km altitude, as shown in FIG. 11. The variable background in CL also means that for accurate measurements on the order of 10 pptv to be made, frequent zero determinations must be performed, and running the instrument for a number of hours before measurements are made is desirable. For this reason, embodiments of the present invention require less effort to operate and has the potential to be more accurate at low mixing ratios for typical aircraft experiments where continuous running prior to flights adds an additional experimental burden.

NO detection apparatus in accordance with embodiments of the present invention can be adapted to a variety of configurations suitable for selective gas detection. Construction of apparatus, as described herein, provides flexibility to vary the shape of NO detection apparatus to fit specific spaces. It is thought that NO detection apparatus of the present invention and many of its attendant advantages will be understood from the foregoing description and it will be apparent that various changes may be made in the form, construction arrangement of parts thereof without departing from the spirit and scope of the invention or sacrificing all of its material advantages, the form hereinbefore described being merely a preferred or exemplary embodiment thereof

What is claimed is:

1. An apparatus for detecting nitric oxide (NO) in a gas sample, said apparatus comprising:
   a first laser source providing a pulsed first laser beam having a first wavelength;
   a fiber optic amplifier system to amplify the pulsed first laser beam, wherein the fiber optic amplifier system maintains spectral purity of the pulsed first laser beam;
   a frequency conversion system to convert the pulsed first laser beam to a fifth harmonic pulsed first laser beam having a second wavelength;
   an optical cell for receiving the gas sample, wherein a longitudinal axis of the optical cell intersects orthogonally with the gas sample flow through the optical cell, wherein the fifth harmonic pulsed first laser beam propagates along the longitudinal axis of the optical cell and intersects the gas sample flow at a first location in the optical cell;
   a second laser source for propagating a second laser beam through the optical cell, wherein the second laser beam intersects orthogonally with the gas sample flow in the optical cell at the first location, wherein the second laser beam photolyzes nitrogen dioxide ($NO_2$) in the gas sample to NO at the first location, wherein the pulsed first laser beam intersecting the gas sample at the first location excites the NO in the gas sample to emit a fluorescence signal; and
   a first photodetector configured to detect the fluorescence signal emitted at the first location in the optical cell.

2. The apparatus of claim 1, further comprising a collimator operatively coupled to receive the pulsed first laser beam from the first laser source, wherein the collimator reduces spatial cross section of the pulsed first laser beam to a predetermined diameter.

3. The apparatus of claim 1, further comprising:
   a first optical lens having an optical axis perpendicular to an optical axis of the pulsed first laser beam, wherein the first optical lens is positioned on a first side of the optical cell to focus the fluorescence signal to the first photodetector;
   a concave mirror for collecting the fluorescence signal, wherein an optical axis of the concave mirror is perpendicular to the optical axis of the pulsed first laser beam, wherein the optical axis of the concave mirror aligns with the optical axis of the first optical lens, wherein the concave mirror is positioned on a second side of the optical cell;
   a second optical lens having an optical axis in alignment with the optical axis of the first optical lens; and
   a bandpass filter positioned between the first and the second optical lens, wherein the bandpass filter is adapted to block the pulsed first laser beam.

4. The apparatus of claim 1, wherein the frequency conversion system further comprises:
   a first optical waveplate to alter a polarization state of the pulsed first laser beam;
   a first non-linear optical crystal positioned to receive the pulsed first laser beam from the first optical waveplate, wherein the first non-linear optical crystal converts the received pulsed first laser beam having the first wavelength to a second harmonic pulsed first laser beam having a third wavelength;
   a second non-linear optical crystal positioned to receive the second harmonic pulsed first laser beam from the first non-linear optical crystal, wherein the second non-linear optical crystal converts the received pulsed first laser beam having the second wavelength to a third harmonic pulsed first laser beam having a fourth wavelength;
   a second optical waveplate positioned to receive the third harmonic pulsed first laser beam from the second non-linear optical crystal, wherein the second optical waveplate rotates residual laser pulses received from the first optical waveplate to align with an axis of the third harmonic pulsed first laser beam received from the second non-linear optical crystal;
a third non-linear optical crystal to provide the fifth harmonic pulsed first laser beam having the second wavelength; and
an optical lens positioned between the second optical waveplate and the third non-linear optical crystal to focus the pulsed first laser beam exiting the second optical waveplate into the third non-linear optical crystal.

5. The apparatus of claim 4, wherein the first non-linear optical crystal is selected from a group comprising potassium titanyl phosphate, periodically poled lithium niobate, or a combination comprising at least one of the foregoing.

6. The apparatus of claim 4, wherein the second non-linear optical crystal is selected from a group comprising lithium triborate, periodically poled lithium niobate, or a combination comprising at least one of the foregoing.

7. The apparatus of claim 4, wherein the third non-linear optical crystal is a beta barium borate crystal.

8. The apparatus of claim 1, wherein the second wavelength of the fifth harmonic pulsed first laser beam is about 215 nm.

9. The apparatus of claim 1, further comprising:
a prism to separate the fifth harmonic pulsed first laser beam received from the frequency conversion system from residual laser pulses;
a plurality of first dielectric mirrors for steering the separated fifth harmonic pulsed first laser beam exiting the prism for a single pass through the optical cell; and
a plurality of second dielectric mirrors for steering the pulsed first laser beam exiting the optical cell, wherein the at least one second dielectric mirror splits the pulsed first laser beam into first and second portions at a predefined power ratio,
wherein the optical cell is disposed between the at least one of the plurality of first dielectric mirrors and the at least one of the plurality of second dielectric mirrors.

10. The apparatus of claim 9, further comprising:
a reference fluorescence cell for receiving a reference gas sample, wherein a longitudinal axis of the reference fluorescence cell intersects orthogonally with the reference gas sample flow in the reference fluorescence cell, wherein the longitudinal axis of the reference fluorescence cell is in alignment with the optical axis of the second portion of the pulsed first laser beam propagating through the reference fluorescence cell; and
a second photodetector for detecting a fluorescence light exiting the reference fluorescence cell.

11. The apparatus of claim 10, further comprising:
a gas sampling system coupled to the optical cell and the reference fluorescence cell, wherein the gas sampling system maintains a predetermined mass flow rate of the gas sample inside the optical cell, wherein the gas sampling system maintains a predetermined mass flow rate of the reference gas sample inside the reference fluorescence cell; and
a controller electrically coupled with the first laser source and the first photon detector, wherein the controller controls timing of the pulsed first laser beam, wherein the controller controls photon detection gating of the first photodetector.

12. The apparatus of claim 1, wherein the first wavelength of the pulsed first laser beam from the first laser source is about 1075 nm.

13. An apparatus for detecting nitric oxide (NO) in a gas sample, said apparatus comprising:
a first laser source providing a pulsed first laser beam having a first wavelength;
a collimator to reduce spatial cross section of the pulsed first laser beam to a predetermined diameter, wherein the collimator is operatively coupled to receive the pulsed first laser beam from the first laser source;
a first optical waveplate operatively coupled to receive the pulsed first laser beam from the collimator, wherein the first optical waveplate alters a polarization state of the pulsed first laser beam received from the collimator;
a first non-linear optical crystal positioned to convert the pulsed first laser beam having the altered polarization state to a second harmonic pulsed first laser beam having a second wavelength, wherein the second wavelength is about one-half of the first wavelength;
a second non-linear optical crystal positioned to convert the second harmonic pulsed first laser beam having the second wavelength to a third harmonic pulsed first laser beam having a third wavelength, wherein the third wavelength is about one-third of the second wavelength;
a third non-linear optical crystal positioned to convert the third harmonic pulsed first laser beam to a fifth harmonic pulsed first laser beam having a wavelength of about 215 nm;
a prism to separate the fifth harmonic pulsed first laser beam received from the third non-linear optical crystal from residual laser pulses;
an optical cell for receiving the gas sample, wherein a longitudinal axis of the optical cell intersects orthogonally with the gas sample flow in the optical cell at a first location, wherein the fifth harmonic pulsed first laser beam propagates through the optical cell, wherein the longitudinal axis of the optical cell is in alignment with an optical axis of the fifth harmonic pulsed first laser beam propagating through the optical cell, wherein the fifth harmonic pulsed first laser beam propagating through the optical cell intersects orthogonally with the gas sample flow in the optical cell;
a second laser source for propagating a second laser beam through the optical cell, wherein the second laser beam intersects orthogonally with the gas sample flow in the optical cell, wherein the second laser beam photolyzes nitrogen dioxide ($NO_2$) in the gas sample to NO at the first location, wherein the pulsed first laser beam intersecting the gas sample at the first location excites the NO in the gas sample to emit a fluorescence signal;
a first optical lens having an optical axis perpendicular to an optical axis of the pulsed first laser beam, wherein the first optical lens is positioned on a first side of the optical cell;
a concave mirror for collecting the fluorescence signal, wherein an optical axis of the concave mirror is perpendicular to the optical axis of the pulsed first laser beam, wherein the optical axis of the concave mirror aligns with the optical axis of the optical lens, wherein the concave mirror is positioned on a second side of the optical cell;
a first photodetector configured to detect a first fluorescence light, wherein the first photodetector is positioned in optical alignment with the concave mirror and the first optical lens;
a reference fluorescence cell for receiving a reference gas sample, wherein a longitudinal axis of the reference fluorescence cell intersects orthogonally with the reference gas sample flowing through the reference fluorescence cell, wherein the longitudinal axis of the reference fluorescence cell is in alignment with the optical axis of at least a portion of the pulsed first laser beam propagating through the reference fluorescence cell; and a second photodetector for detecting a second fluorescence light exiting the reference fluorescence cell.

14. The apparatus of claim 13, wherein the frequency conversion system further comprises:
a second optical waveplate positioned to receive the third harmonic pulsed first laser beam from the second non-linear optical crystal, wherein the third harmonic pulsed first laser beam comprises residual laser pulses from the first optical waveplate, wherein the second optical waveplate rotates the residual laser pulses from the first optical waveplate to align an axis of the residual laser pulses parallel to an axis of the third harmonic pulsed first laser beam received from the second non-linear optical crystal; and
an optical lens positioned between the second optical waveplate and the third non-linear optical crystal to focus the pulsed first laser beam exiting the second optical waveplate into the third non-linear optical crystal.

15. The apparatus of claim 13, further comprising:
a plurality of first dielectric mirrors for steering the separated fifth harmonic pulsed first laser beam exiting the prism for a single pass through the optical cell;
a plurality of second dielectric mirrors for steering the pulsed first laser beam exiting the optical cell, wherein the at least one second dielectric mirror splits the pulsed first laser beam into first and second portions at a predefined power ratio; and
a solar-blind power monitoring phototube for measuring the first portion of the pulsed first laser beam exiting the laser induced fluorescence cell,
wherein the optical cell is disposed between the at least one of the plurality of the first dielectric mirror and the at least one of the plurality of the second dielectric mirrors.

16. The apparatus of claim 13, further comprising:
a second optical lens having an optical axis in alignment with the optical axis of the first optical lens; and
a bandpass filter positioned between the first and the second optical lens, wherein the bandpass filter is adapted to block the pulsed first laser beam.

17. The apparatus of claim 13, further comprising:
a gas sampling system coupled to the optical cell and the reference fluorescence cell, wherein the gas sampling system maintains a predetermined mass flow rate of the gas sample inside the optical cell, wherein the gas sampling system maintains a predetermined mass flow rate of the reference gas sample inside the reference fluorescence cell; and
a controller electrically coupled with the laser source and the first photon detector, wherein the controller controls timing of the pulsed first laser beam, wherein the controller controls photon detection gating of the first photon detector.

18. The apparatus of claim 13, wherein the pulsed first laser beam from the laser source has a wavelength of about 1075 nm.

19. A method for detecting nitric oxide (NO) in a gas sample, said method comprising:
generating an amplified pulsed first laser beam having a first wavelength and a second laser beam having a second wavelength;
reducing spatial cross section of the pulsed first laser beam to a predetermined diameter;
altering a polarization state of the pulsed first laser beam;
converting the pulsed first laser beam to a fifth harmonic pulsed first laser beam having a third wavelength;
optically transmitting the fifth harmonic pulsed first laser beam having the third wavelength through the gas sample flowing orthogonally to an axis of the fifth harmonic pulsed first laser beam, wherein the fifth harmonic pulsed first laser beam intersects the gas sample at a first location, wherein the fifth harmonic pulsed first laser beam intersecting the gas sample excites the NO in the gas sample to emit a fluorescence light;
optically transmitting the second laser beam having the second wavelength orthogonally through the gas sample flowing to photolyze nitrogen dioxide ($NO_2$) in the gas sample to NO, wherein the second laser beam intersects the gas sample at the first location;
detecting the fluorescence light emitted from the first location; and
analyzing the detected fluorescence light to detect the NO in the gas sample.

20. The method of claim 19, wherein the wavelength of the fifth harmonic pulsed first laser beam is about 215 nm.

* * * * *